(12) United States Patent
Krishnaswamy et al.

(10) Patent No.: US 8,329,168 B2
(45) Date of Patent: Dec. 11, 2012

(54) COMPOSITIONS AND METHODS FOR MODULATING HEMOSTASIS

(75) Inventors: Sriram Krishnaswamy, St. Davids, PA (US); Elsa P. Bianchini, Villebon/Yvette (FR); Steven Orcutt, Audubon, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 742 days.

(21) Appl. No.: 12/093,787

(22) PCT Filed: Nov. 15, 2006

(86) PCT No.: PCT/US2006/060924
§ 371 (c)(1),
(2), (4) Date: Sep. 5, 2008

(87) PCT Pub. No.: WO2007/059511
PCT Pub. Date: May 24, 2007

(65) Prior Publication Data
US 2009/0081280 A1   Mar. 26, 2009

Related U.S. Application Data

(60) Provisional application No. 60/736,784, filed on Nov. 15, 2005.

(51) Int. Cl.
*A61K 38/48* (2006.01)
*C07H 21/02* (2006.01)
(52) U.S. Cl. .................................. 424/94.64; 536/23.1
(58) Field of Classification Search ...................... None
See application file for complete search history.

(56) References Cited

U.S. PATENT DOCUMENTS

| 4,207,232 A | 6/1980 | Claeson et al. |
| 2003/0099957 A1 | 5/2003 | McCarthy |
| 2004/0120943 A1 | 6/2004 | Gruber et al. |

OTHER PUBLICATIONS

Gan et al., Arch. Biochem. Biophys., 1993, 302: 228-236, Abstract.*
Bianchini et al., Proc Natl Acad Sci USA, Jul. 19, 2005, 102: 10099-10104.*
Orcutt et al., J Biol Chem, 2004, 279: 54927-54936.*
Bianchini, E., et al. "Ratcheting of the substrate from the zymogen to proteinase conformations directs the sequential cleavage of prothrombin by prothrombinase." PNAS, 102(29): 10099-10104 (Jul. 19, 2005).

* cited by examiner

*Primary Examiner* — Ileana Popa
(74) *Attorney, Agent, or Firm* — Dann, Dorfman, Herrell & Skillman; Kathleen D. Rigaut

(57) ABSTRACT

Novel thrombin/prothrombin protease/zymogen variants which have anticoagulation activity and methods of use thereof are disclosed.

9 Claims, 10 Drawing Sheets

Fig. 8A
Human Prothrombin

Fig 8B

```
 901 TTGTGAGGAG GCCGTGGAGG AGGAGACAGG AGATGGGCTG GATGAGGACT CAGACAGGGC CATGGAAGGG CGTACCGCCA CCAGTGAGTA CCAGACTTTC
     AACACTCCTC CGGCACCTCC TCCTCTGTCC TCTACCCGAC CTACTCCTGA GTCTGTCCCG GTAGCTTCCC GCATGGCGGT GGTCACTCAT GGTCTGAAAG
      F  N  P  R  T  F  G  G  S  G  E  A  D  C  G  L  R  P  L  F  E  K  K  S  L  E  D  K  T  E  R  E  L  L  E  .

1001 TTCAATCCGA GGACCTTTGG CTCGGGAGAG GCAGAGACTGTG GCTGCGACC TCTCTTCGAG AAGAAGTCGC TGGAGGACAA AACCGAAAGA GAGCTCCTGG
     AAGTTAGGCT CCTGGAAACC GAGCCCTCC CGTCGACAC CGAGCGCTGG AGACAAGCTC TTCTTCAGCG ACCTCCTGTT TTGGCTTTCT CTCGAGGACC
                                                      | Thrombin B Chain (Protease Domain) Start
      .  S  Y  I  D  G  R     G  S  D  A  E  I  G  M  S  P  W  Q  V  M  L  F  R  K  S  P  Q  E  L  L  .

1101 AATCCTACAT CGACGGGCGC ATTGTGAGG GCTGGGATGC AGAGATCGGC ATGTCACCTT GGCAGGTGAT GCTTTTCCGG AAGAGCCCCC AGGAGCTGCT
     TTAGGATGTA GCTGCCCGCG TAACACCTCC CGACCCTACG TCTCTAGCCG TACAGTGGAA CCGTCCACTA CGAAAAGGCC TTCTCGGGGG TCCTCGACGA
      .  C  G  A  S  L  I  S  D  R  W  V  L  T  A  A  H  C  L  L  Y  P  P  W  D  K  N  F  T  E  N  D  L  L  .

1201 GTGTGGGGCC AGCCTCATCA GTGACCGCTG GGTCCTCACC GCCGCCCACT GCCTCCTGTA CCCGCCCTGG GACAAGAACT TCACCGAGAA TGACCTTCTG
     CACACCCCGG TCGGAGTAGT CACTGGCGAC CCAGGAGTGG CGGCGGGTGA CGGAGGACAT GGGCGGGACC CTGTTCTTGA AGTGGCTCTT ACTGGAAGAC
      .  V  R  I  G  K  H  S  R  T  R  Y  E  R  N  I  E  K  I  S  M  L  E  K  I  Y  I  H  P  R  Y  N  W  R  E  .

1301 GTCCGCATTG GCAAGCACTC CCGGACCAGG TACGAGCGAA ACATTGAAAA GATATCCATG CTGGAAAAGA TCTACATCCA CCCCAGGTAC AACTGGCGGG
     CAGGCGTAAC CGTTCGTGAG GGCCTGGTCC ATGCTCGCTT TGTAACTTTT CTATAGGTAC GACCTTTTCT AGATGTAGGT GGGGTCCATG TTGACCGCCC
      .  N  L  D  R  D  I  A  L  M  K  L  K  K  P  V  A  F  S  D  Y  I  H  P  V  C  L  P  D  R  E  T  A  A  .

1401 AGAACCTGGA CCGGGACATT GCCCTGATGA AGCTGAAGAA AGCTGTTGCC TTCAGTGACT ACATTCACCC TGTGTGTCTG CCCGACAGGG AGACGGCAGC
     TCTTGGACCT GGCCCTGTAA CGGGACTACT TCGACTTCTT CGACAACGG AAGTCACTGA TGTAAGTGGG ACACACAGAC GGGCTGTCCC TCTGCCGTCG
      .  S  L  L  Q  A  G  Y  K  G  R  V  T  G  W  G  N  L  K  E  T  W  T  A  N  V  G  K  G  Q  P  S  V  L  .

1501 CAGCTTGCTC CAGGGCTGGAT ACAAGGGGCG GGTGACAGGC TGAAGGAGAC GTGGACAGCC AACGTTGGTA AGGGGCAGCC CAGTGTTCTG
     GTCGAACGAG GTCCGACCTA TGTTCCCCGC CCACTGTCCG ACCTTCCTCTG ACTTCCTCTG TTGCAACCAT TCCCCGTCGG GTCACAGGAC
      .  Q  V  V  N  L  P  I  V  E  R  P  V  C  K  D  S  T  R  I  R  I  T  D  N  M  F  C  A  G  Y  K  P  D  E  .

1601 CAGGTGGTGA ACCTGCCCAT TGTGGAGCGG CCGGTCTGCA AGGACTCCAC CCGTATCCGC ATCACTGACA ACATGTTCTG TGCTGGTTAC AAGCCTGATG
     GTCCACCACT TGGACGGGTA ACACCCTCGCC GGCCAGACGT TCCTGAGGTG GGCATAGGCG TAGTGACTGT TGTACAAGAC ACGACCAATG TTCGGACTAC
      .  G  K  R  G  D  A  C  E  G  D  S  G  G  P  F  V  M  K  S  P  F  N  N  R  W  Y  Q  M  G  I  V  S  W  .

1701 AAGGAAACG AGGGATGCC TGTGAAGTG ACAGTGGGGG ACACTTCCAC TGTCACCCAC TGGAAAACAG TACTTCTCGG CCGCTGGTAT CAAATGGGCA TCGTCTCATG
     TTCCCTTTGC TCCCCTACGG ACACTTCAC ACACTTCCAC TGTCACCCAC ACCTTTGTCG GGAAATTGTT TTGGCGGACCATA GTTTACCCGT AGCAGAGTAC
      .  G  E  G  C  D  R  D  G  K  Y  G  F  Y  T  H  V  F  R  L  K  K  W  I  Q  K  V  I  D  Q  F  G  E  *  .

1801 GGGTGAAGGC TGTGACCGGG ATGGAAATA TGGCTTCTAC ACACATGTGT TCCGCCTGAA GAAGTGGATA TTGATCAGTT TGGAGAGTAG
     CCCACTTCCG ACACTGGCCC TACCCTTTAT ACCGAAGATG TGTGTACACA AGGCGGACTT CTTCACCTAT AACTAGTCAA ACCTCTCATC
```

Fig. 8C
1901 TGATAACTCG AGGTACCGGA TCCTGGAACC AATCCCGTGA AAGAATTATT TTTGTGTTTC TAAAACTATG GTTCCCAATA AAAGTGACTC TCAGCGG
     ACTATTGAGC TCCATGGCCT AGGACCTTGG TTAGGGCACT TTCTTAATAA AAACACAAAG ATTTTGATAC CAAGGGTTAT TTTCACTGAG AGTCGCC

US 8,329,168 B2

COMPOSITIONS AND METHODS FOR MODULATING HEMOSTASIS

The present application is §371 application of PCT/US2006/060924 filed 15 Nov. 2006 which claims priority to U.S. 60/736,784 filed 15 Nov. 2005, the entire disclosure of each being incorporated by reference herein.

This application claims priority under 35 U.S.C. §119(e) to U.S. Provisional Application No. 60/736,784 filed Nov. 15, 2005, the entire contents being incorporated by reference herein as though set forth in full.

Pursuant to 35 U.S.C. §202(c), it is acknowledged that the U.S. Government has certain rights in the invention described herein, which was made in part with funds from the National Institutes of Health, Grant Numbers PO1 HL-74124, and HL-47465.

FIELD OF THE INVENTION

The present invention relates to the fields of medicine and hematology. More specifically, the invention provides novel prothrombin/thrombin coagulation agents and methods of using the same to modulate the coagulation cascade in patients in need thereof.

BACKGROUND OF THE INVENTION

Several publications and patent documents are cited throughout the specification in order to describe the state of the art to which this invention pertains. Each of these citations is incorporated herein by reference as though set forth in full.

The enzymes of coagulation are trypsin-like enzymes that belong to the S1 peptidase family of proteases that bear a chymotrypsin-like fold. The coagulation proteases contain catalytic domains that are highly homologous to each other and to the ancestral serine proteases of digestion. The structural homology/identity is so great (>70%) that residues in the catalytic domains of the coagulation enzymes are numbered according to the corresponding residues in chymotrypsinogen.

The coagulation enzymes circulate in blood as inactive precursors, zymogens, that require proteolytic cleavage for activation. The zymogens possess ~10,000-fold or less proteolytic activity when compared to the serine proteases produced following activation. Initiation of coagulation at the site of vascular damage leads to a series of reactions in which a zymogen is converted to a protease through specific proteolytic cleavage and forms the enzyme for the successive reaction. This culminates in blood cell activation and the conversion of soluble fibrinogen to insoluble fibrin and hence the formation of the clot. Excess proteases are removed by reaction with circulating protease inhibitors that act as "suicide" substrates or those that recognize the active enzymes. Thus, proteolytic activation of the coagulation zymogens is a key regulatory feature of the coagulation cascade.

Although some of the coagulation zymogens are cleaved at two or more sites in their respective activation reactions, only one of these cleavage reactions is necessary for protease formation. Cleavage at this site and its structural consequences are considered in the most facile way using the homologous numbering system based on chymotrypsinogen and the extensive structural work done with trypsinogen and trypsin. The conversion of the zymogen to serine protease requires cleavage following $Arg^{15}$ (typically the bond between $Arg^{15}$ and $Ile^{16}$) which exposes a new N-terminus in the catalytic domain beginning with $Ile^{16}$. In trypsin the new N-terminal sequence begins with $Ile^{16}$-$Val^{17}$-$Gly^{18}$-$Gly^{19}$ (SEQ ID NO: 4). For the clotting enzymes, the new N-terminal sequence is a variation on the same theme. The N-terminal sequence then folds back into the catalytic domain and inserts into the N-terminal binding cleft in a sequence-specific manner which is referred to as "molecular sexuality". Accordingly, variants with alternate N-terminal sequences are not likely to undergo molecular sexuality in a comparable way. N-terminal insertion leads to the formation of a salt bridge between the $\alpha$-$NH_2$ group of $Ile^{16}$ and $Asp^{194}$ in the interior of the catalytic domain. Salt bridge formation is associated with numerous changes in catalytic domain structure including: rearrangements of the so-called activation domains; formation of the oxyanion hole required for catalysis and the formation of a substrate binding site. These changes lead to the maturation of the active serine protease. The key contribution of sequence-specific interactions of the new N-terminus through molecular sexuality and salt bridge formation to the maturation of the active protease are evident from the following facts: bacterial proteases that do not require cleavage for activation utilize another side-chain within the catalytic domain to salt bridge with $Asp^{194}$; trypsinogen can be activated to a proteinase-like conformation without cleavage but with extremely high concentrations of an Ile-Val dipeptide that inserts into the cleft, albeit very inefficiently; the Val-Ile dipeptide and other variants are far less effective; additionally, there are two examples of bacterial proteins that activate coagulation zymogens in the absence of cleavage by subverting the activation mechanism via provision of their own N-terminus that inserts into the N-terminal binding cleft.

The structural changes outlined above provide a molecular explanation for the conversion of a precursor zymogen to an active serine protease. However, unlike trypsin which is fully active following cleavage at $Arg^{15}$, many of the coagulation enzymes act very poorly on their protein substrates. Even though they generally possess fully functional active sites and can cleave small peptidyl substrates, efficient cleavage of the biological substrate often requires a cofactor protein. In these cases, the cofactor proteins increase the rate of protein substrate cleavage by several thousand fold. Although the mechanism by which the cofactor proteins function remains to be resolved, they are unlikely to function by making the protease more enzyme-like and therefore more efficient. A key point is that, with one exception, the cofactors selectively bind the protease and not the corresponding zymogen.

Depending on the state of the patient it may be desirable to develop altered coagulation cascade proteins which possess enhanced or reduced coagulation function. It is an object of the invention to provide such proteins for use as therapeutics.

SUMMARY OF THE INVENTION

In accordance with the present invention, compositions and methods are provided for influencing regulatory sites in the procofactor/zymogen→cofactor/protease transition pathway thereby modulating rate and specificity of the cleavage reaction. The compositions and methods of the invention are effective to modulate hemostasis in patients in need thereof.

In one embodiment a variant thrombin zymogen/protease which modulates hemostasis is provided having SEQ ID NO: 1, wherein each X at the thrombin B chain protease domain start (e.g., amino acids at positions 321, 322 and 323) can be any amino acid. See FIG. 8. Also provided is a nucleic acid encoding said thrombin variant. Such nucleic acids may optionally encode an intracellular PACE/furin cleavage site to facilitate production of the "activated" polypeptide. Particularly preferred are nucleic acids wherein the nucleotides at positions 1122-1131 of SEQ ID NO: 2 encode amino acids selected from the group consisting of Val-Ile-Glu, Ile-Glu-Gly and Thr-Ala-Thr. Host cells expressing these nucleic acids are also within the scope of the invention.

In yet another aspect, a pharmaceutical composition having anticoagulant properties comprising the thrombin variants disclosed herein in a biologically compatible carrier is provided. Such variants may be administered directly or the nucleic acids encoding the same may be inserted into an expression vector. Administration of such vectors to a patient in need thereof results in the expression of therapeutic levels of the prothrombin/thrombin variants described herein.

Thus, in yet another embodiment of the invention, a method for treatment of a hemostasis related disorder in a patient in need thereof comprising administration of a therapeutically effective amount of the thrombin variant in a biologically acceptable carrier is provided. Such disorders, include, without limitation, thrombosis, thrombocytopenia, stroke, and coagulapathy.

BRIEF DESCRIPTION OF THE DRAWINGS

Figure 8A:
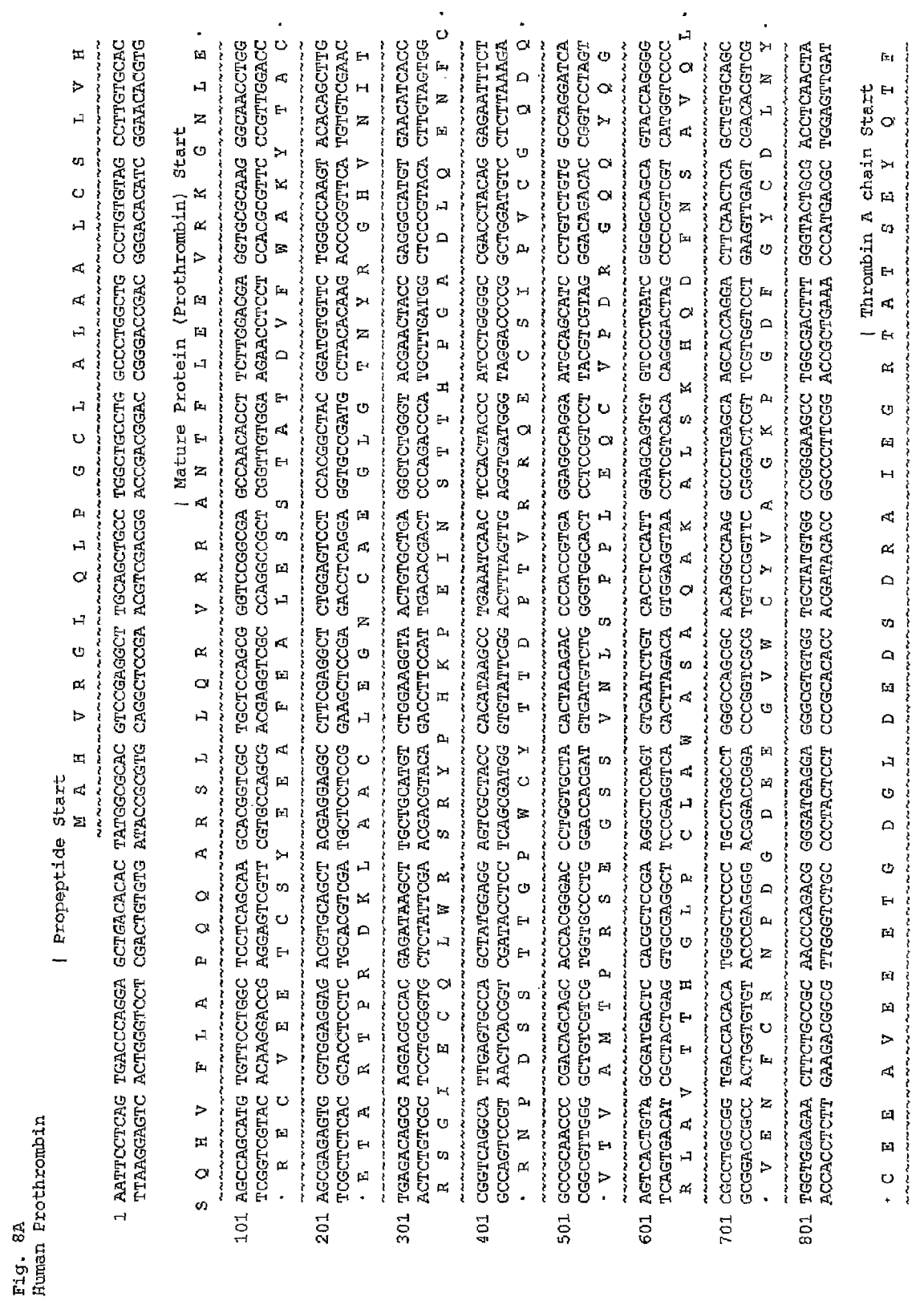

FIG. 8. The amino acid (SEQ ID NO: 1) and nucleic acid (SEQ ID NO: 2) sequences encoding thrombin.

DETAILED DESCRIPTION OF THE INVENTION

Figure 1:
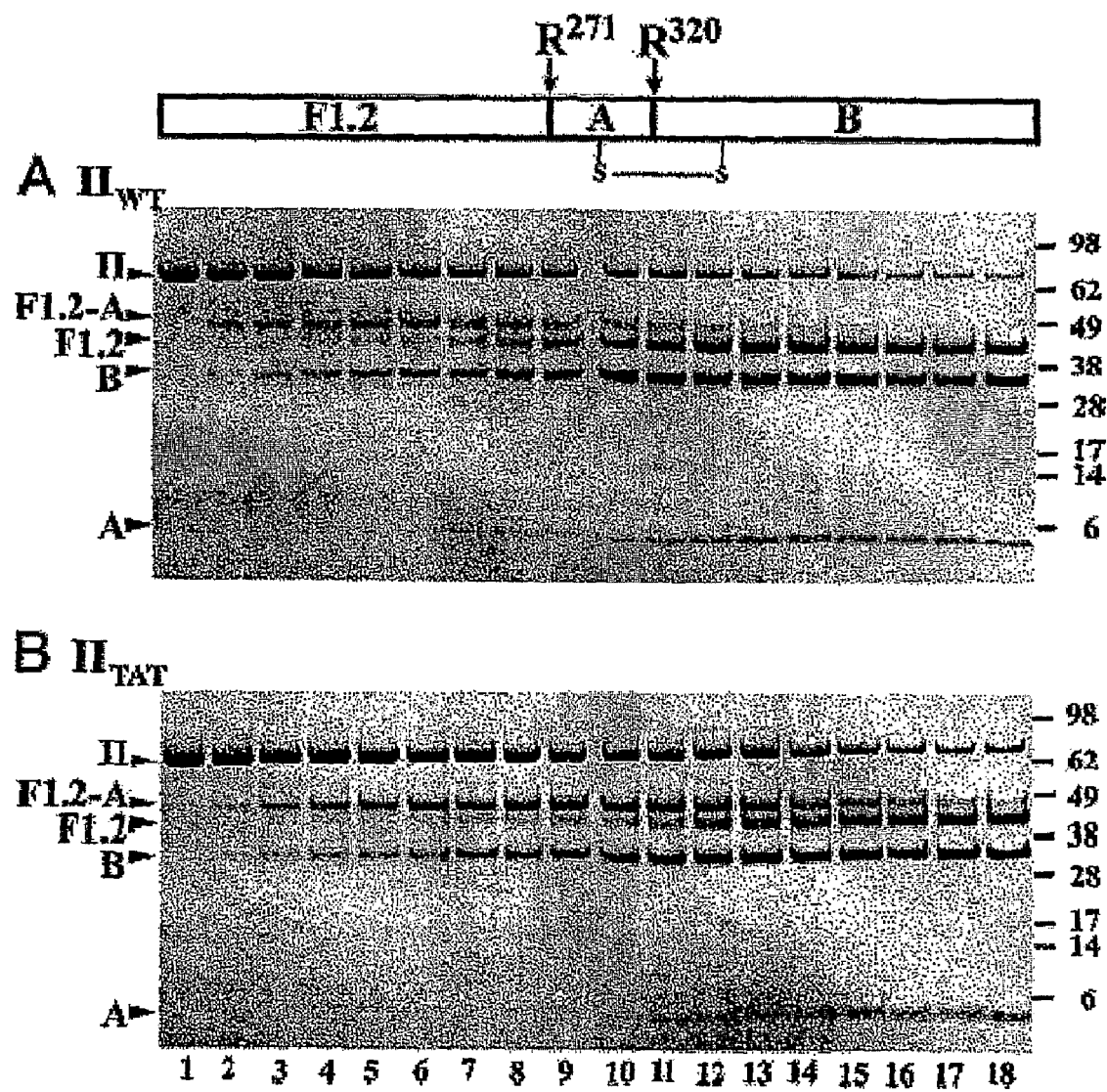
FIG. 1. Cleavage of prothrombin variants by prothrombinase. The indicated prothrombin derivatives (5.4 μM) were digested by 0.8 nM prothrombinase (0.8 nM Xa/28 mM Va/20 μM PCPS). $II_{WT}$ (A) was activated in the presence of 60 μM DAPA, and $II_{TAT}$ (B) was activated in the absence of DAPA. Serially quenched samples were analyzed by SDS PAGE (4.2 μg per lane) after disulfide bond reduction. Lanes 1-18 correspond to reaction times of 0, 0.33, 0.67, 1, 1.33, 1.67, 2, 2.5, 3, 3.5, 4, 6, 8, 12, 16, 20, 26, and 32 min. The margins indicate molecular weights (×10³) of the markers and the migration positions of relevant prothrombin fragments. The relationship between the two cleavage sites and the relevant prothrombin fragments is schematically illustrated at the top of the figure.

Proteolysis is an essential aspect of blood coagulation and underlies many of the mechanisms regulating normal hemostasis. Procofactors and zymogens cannot participate to any significant degree in their respective macromolecular enzymatic complexes. This indicates that proteolytic activation must result in appropriate structural changes that lead to the expression of sites which impart enzyme, substrate and cofactor binding capabilities. While procofactor and zymogen activation has been intensively studied, the relationship between proteolysis and the expression of binding sites which impart function is incompletely understood. The present invention provides model compositions and systems which elucidate the molecular mechanisms underlying the expression of macromolecular binding interactions that accompany transitions from the procofactor and zymogen states.

Thrombin is a key serine protease product of coagulation because it catalyses the reactions associated with the formation of the clot. Thrombin is a key regulatory product because it also catalyses reactions that are important for enhancing clot formation in the initial stages of the clotting process and inhibiting the reactions of the cascade in the later stages. As with all other coagulation proteases, the active thrombin concentration available to participate in these different functions is determined by its reaction and elimination by protease inhibitors that circulate in plasma. Unlike other coagulation enzymes, thrombin does not require a cofactor to accomplish most of these functions. However, the cofactor protein, thrombomodulin (TM), is essential for the anticoagulant function of thrombin in the production of activated protein C. Thrombin by itself is a profoundly poor activator of protein C. The rate of activated protein C formation is greatly increased upon the binding of thrombin to thrombomodulin while all the other activities of thrombin are inhibited.

Changes to the N-terminal sequence (Ile-Val-Glu) following the Arg15 cleavage site that lead to suboptimal molecular sexuality are expected to yield a "zymogen-like" thrombin derivative that has impaired, or even zero, proteolytic activity. This will diminish all functions of thrombin that rely on its proteolytic activity. However, thrombin, but not its prothrombin precursor, binds tightly to TM. Furthermore, in the large repertoire of thrombin substrates and ligands, TM is the tightest binding partner for thrombin and its concentration in the microcirculation is expected to be very high. It follows from the laws of thermodynamics that TM should bind more weakly to the impaired "zymogen-like" thrombin form but also affect rescue of its catalytic activity. Because thrombin bound to TM selectively functions as an anticoagulant by catalyzing APC formation, it follows that TM-mediated rescue will selectively impart anticoagulant function to the impaired "zymogen-like" form. Because thrombin active site function is required for the reaction of thrombin with circulating protease inhibitors (Serpins), the impaired thrombin is expected to be refractory to elimination by inhibition and is therefore expected to be long lived in the circulation. Thus, zymogen-like forms of thrombin may be powerful anticoagulants that are persistent in blood following infusion. Alternatively, prothrombin derivatives that yield a zymogen-like form of thrombin are expected to be cleaved normally upon physiological activation of coagulation but persist in circulation with anticoagulant function.

I. DEFINITIONS

Various terms relating to the biological molecules of the present invention are used hereinabove and also throughout the specification and claims.

The phrase "variant zymogen/protease" refers to a modified prothrombin/thrombin which has been genetically altered such that its protease activity is reduced or enhanced. The "variant zymogen/protease" can either be cleaved in vitro to a protease with altered function or alternatively may be cleaved following the endogenous activation of coagulation in human blood to yield a product with reduced or enhanced activity. Preferred sites for amino acid alterations in the parent thrombin molecule include modifying the codons at positions 1122-1131 to encode a tripeptide selected from the group consisting of Thr-Ala-Thr, Val-Ile-Glu and Ile-Glu-Gly. These tripeptides occur at positions 321, 322 and 323 of SEQ ID NO: 1 respectively.

The phrase "hemostasis related disorder" refers to bleeding disorders such as thrombosis related diseases including deep venous thrombosis, thrombosis associated with cardiovascular disease states or malignancies, thrombosis resulting from in-dwelling catheters or other invasive surgical procedures and thrombosis associated with autoimmune diseases such as lupus. The zymogen/protease variants could also provide necessary anticoagulant treatment for patients with disseminated intravascular coagulation or consumptive coagulopathies arising from a variety of disease states. Thrombin variants could also be useful for providing anticoagulant unction in heparin induced thrombocytopenia when heparin is no longer effective.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "promoter region" refers to the transcriptional regulatory regions of a gene, which may be found at the 5' or 3' side of the coding region, or within the coding region, or within introns.

The term "vector" refers to a small carrier DNA molecule into which a DNA sequence can be inserted for introduction into a host cell where it will be replicated. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, of the compound of interest. Purity is measured by methods appropriate for the compound of interest (e.g. chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO:. For example, when used in reference to an amino acid sequence, the phrase includes the sequence per se and molecular modifications that would not affect the basic and novel characteristics of the sequence.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application for which the oligonucleotide is used.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15-25 or more nucleotides, although it may contain fewer nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under predetermined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to act functionally as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirements of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "percent identical" is used herein with reference to comparisons among nucleic acid or amino acid sequences. Nucleic acid and amino acid sequences are often compared using computer programs that align sequences of nucleic or amino acids thus defining the differences between the two. For purposes of this invention comparisons of nucleic acid sequences are performed using the GCG Wisconsin Package version 9.1, available from the Genetics Computer Group in Madison, Wis. For convenience, the default parameters (gap creation penalty=12, gap extension penalty=4) specified by that program are intended for use herein to compare sequence identity. Alternately, the Blastn 2.0 program provided by the National Center for Biotechnology Information (on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences.

II. PREPARATION OF VARIANT ZYMOGEN-PROTEASE ENCODING NUCLEIC ACID MOLECULES AND POLYPEPTIDES

A. Nucleic Acid Molecules

Nucleic acid molecules encoding the variant zymogen/proteases of the invention may be prepared by using recombinant DNA technology methods. The availability of nucleotide sequence information enables preparation of isolated nucleic acid molecules of the invention by a variety of means. For example, nucleic acid sequences encoding a zymogen/protease polypeptide may be isolated from appropriate biological sources using standard protocols well known in the art.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Alternatively, the nucleic acids may be maintained in vector suitable for expression in mammalian cells. In cases where post-translational modification affects zymogen/protease function (e.g., thrombin), it is preferable to express the molecule in mammalian cells.

In one embodiment, the nucleic acids encoding the prothrombin/thrombin zymogen variants may be further modified via insertioll of an intracellular proteolytic cleavage site. In order to express "activated" zymogen-like thrombin variants in mammalian cells, an intracellular proteolytic cleavage site can be inserted between positions Arg320 and Ile 321 in the variant thrombin zymogen. Such cleavage sites include: Arg-Lys-Arg or Arg-Lys-Arg-Arg-Lys-Arg (SEQ ID NO: 5). These cleavage sites are efficiently recognized by proteases (PACE/furin-like enzymes) within the cell and are removed. This results in a processed variant thrombin in which the heavy chain on the molecule begins now begins at position 321. Introduction of this cleavage site at said position will allow for the intracellular conversion of prothrombin to thrombin.

Ultimately these types of modifications allow for secretion of the "active" processed form of variant thrombin from a cell that expresses the modified variant thrombin. Secretion of the cleaved factor obviates a need for proteolytic cleavage during blood clotting or following the isolation of the protein.

Variant zymogen/protease-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting zymogen/protease expression.

B. Proteins

A full-length variant zymogen/protease polypeptide of the present invention may be prepared in a variety of ways, according to known methods. The prothrombin/thrombin variant can either be supplied as the cleaved final product or as the uncleaved precursor which will be acted upon in the body. The protein may be purified from appropriate sources, e.g., transformed bacterial or animal cultured cells or tissues which express zymogen/protease, by immunoaffinity purification. However, this is not a preferred method due to the low amount of protein likely to be present in a given cell type at any time.

The availability of nucleic acid molecules encoding a variant zymogen/protease polypeptide enables production of zymogen/protease using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of zymogen/protease may be produced by expression in a suitable prokaryotic or eukaryotic expression system. For example, part or all of a DNA molecule encoding variant thrombin for example, may be inserted into a plasmid vector adapted for expression in a bacterial cell, such as *E. coli* or a mammalian cell such as CHO or Hela cells. Alternatively, in a preferred embodiment, tagged fusion proteins comprising zymogen/protease can be generated. Such zymogen/protease-tagged fusion proteins are encoded by part or all of a DNA molecule, ligated in the correct codon reading frame to a nucleotide sequence encoding a portion or all of a desired polypeptide tag which is inserted into a plasmid vector adapted for expression in a bacterial cell, such as *E. coli* or a eukaryotic cell, such as, but not limited to, yeast and mammalian cells. Vectors such as those described above comprise the regulatory elements necessary for expression of the DNA in the host cell positioned in such a manner as to permit expression of the DNA in the host cell. Such regulatory elements required for expression include, but are not limited to, promoter sequences, transcription initiation sequences, and enhancer sequences.

Variant zymogen/protease proteins, produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope, GST or the hemagglutinin epitope. Such methods are commonly used by skilled practitioners.

Zymogen/protease proteins, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. A variety of expression systems of utility for the methods of the present invention are well known to those of skill in the art.

Accordingly, the present invention also encompasses a method of making a polypeptide (as disclosed), the method including expression from nucleic acid encoding the polypeptide (generally nucleic acid). This may conveniently be achieved by culturing a host cell, containing such a vector, under appropriate conditions which cause or allow production of the polypeptide. Polypeptides may also be produced in in vitro systems, such as reticulocyte lysate.

III. USES OF ZYMOGEN/PROTEASE-ENCODING NUCLEIC ACIDS AND PROTEINS

Variant zymogen/protease nucleic acids encoding polypeptides having altered protease activities with the potential of being activated in human blood to yield a product with altered protease activity may be used according to this invention, for example, as therapeutic and/or prophylactic agents which modulate the blood coagulation cascade. The present inventors have discovered that zymogen/protease molecules can be altered to decrease coagulation.

A. Variant Zymogen/Protease Polypeptides

Variant zymogen/protease thrombin polypeptides may be used for a variety of purposes in accordance with the present invention. In a preferred embodiment of the present invention, variant zymogen/protease polypeptides may be administered to a patient via infusion in a biologically compatible carrier. The variant zymogen/proteases of the invention may optionally be encapsulated in to liposomes or other phospholipids to increase stability of the molecule. Zymogen/protease may be administered alone or in combination with other agents known to modulate hemostasis. An appropriate composition in which to deliver zymogen/protease polypeptides may be determined by a medical practitioner upon consideration of a variety of physiological variables, including, but not limited to, the patient's condition and hemodynamic state. A variety of compositions well suited for different applications and routes of administration are well known in the art and described hereinbelow.

The preparation containing the purified prothrombin/thrombin variant contains a physiologically acceptable matrix and is preferably formulated as a pharmaceutical preparation. The preparation can be formulated using substantially known prior art methods, it can be mixed with a buffer containing salts, such as NaCl, $CaCl_2$, and amino acids, such as glycine and/or lysine, and in a pH range from 6 to 8. Until needed, the purified preparation containing the prothrombin or thrombin variant can be stored in the form of a finished solution or in lyophilized or deep-frozen form. Preferably the preparation is stored in lyophilized form and is dissolved into a visually clear solution using an appropriate reconstitution solution.

Alternatively, the preparation according to the present invention can also be made available as a liquid preparation or as a liquid that is deep-frozen.

The preparation according to the present invention is especially stable, i.e., it can be allowed to stand in dissolved form for a prolonged time prior to application.

The preparation according to the present invention can be made available as a pharmaceutical preparation with thrombin activity in the form of a one-component preparation or in combination with other factors in the form of a multi-component preparation.

Prior to processing the purified protein into a pharmaceutical preparation, the purified protein is subjected to the conventional quality controls and fashioned into a therapeutic form of presentation. In particular, during the recombinant manufacture, the purified preparation is tested for the absence of cellular nucleic acids as well as nucleic acids that are derived from the expression vector, preferably using a method, such as is described in EP 0 714 987.

Another feature of this invention relates to making available a preparation which contains a prothrombin/thrombin variant with a high stability and structural integrity and which, in particular, is free from inactive thrombin intermediates and autoproteolytic degradation products and which can be produced by activating a thrombin variant of the type described above and by formulating it into an appropriate preparation.

The pharmaceutical preparation may contain dosages of between 10-1000 μg/kg, more preferably between about 10-250 μg/kg and most preferably between 10 and 75 μg/kg, with 40 μg/kg of the variant thrombin polypeptide being particularly preferred. Patients may be treated immediately upon presentation at the clinic with a coagulation disorder. Alternatively, patients may receive a bolus infusion every one to three hours, or if sufficient improvement is observed, a once daily infusion of the variant thrombin polypeptide described herein.

B. Zymogen/Protease-Encoding Nucleic Acids

Zymogen/protease-encoding nucleic acids may be used for a variety of purposes in accordance with the present invention. In a preferred embodiment of the invention, a nucleic acid delivery vehicle (i.e, an expression vector) for modulating blood coagulation is provided wherein the expression vector comprises a nucleic acid sequence coding for a variant zymogen/protease polypeptide, or a functional fragment thereof as described herein. Administration of zymogen/protease-encoding expression vectors to a patient results in the expression of zymogen/protease polypeptide which serves to alter the coagulation cascade. In accordance with the present invention, an zymogen/protease encoding nucleic acid sequence may encode an zymogen/protease polypeptide as described herein whose expression either increases or decreases hemostasis. In a preferred embodiment, a zymogen/protease nucleic acid sequence encodes a human thrombin polypeptide variant.

Expression vectors comprising variant zymogen/protease nucleic acid sequences may be administered alone, or in combination with other molecules useful for modulating hemostasis. According to the present invention, the expression vectors or combination of therapeutic agents may be administered to the patient alone or in a pharmaceutically acceptable or biologically compatible compositions.

In a preferred embodiment of the invention, the expression vector comprising nucleic acid sequences encoding the variant zymogen/protease variants is a viral vector. Viral vectors which may be used in the present invention include, but are not limited to, adenoviral vectors (with or without tissue specific promoters/enhancers), adeno-associated virus (AAV) vectors of multiple serotypes (e.g., AAV-2, AAV-5, AAV-7, and AAV-8) and hybrid AAV vectors, lentivirus vectors and pseudo-typed lentivirus vectors [e.g., Ebola virus, vesicular stomatitis virus (VSV), and feline immunodeficiency virus (FIV)], herpes simplex virus vectors, vaccinia virus vectors, and retroviral vectors.

In a preferred embodiment of the present invention, methods are provided for the administration of a viral vector comprising nucleic acid sequences encoding a variant zymogen/protease, or a functional fragment thereof. Adenoviral vectors of utility in the methods of the present invention preferably include at least the essential parts of adenoviral vector DNA. As described herein, expression of a variant zymogen/protease polypeptide following administration of such an adenoviral vector serves to modulate hemostasis. In the context of the variant thrombin described herein, such administration enhances the procoagulation activity of the protease. The variant thrombin molecule described herein may be used to advantage as an anticoagulant.

Recombinant adenoviral vectors have found broad utility for a variety of gene therapy applications. Their utility for such applications is due largely to the high efficiency of in vivo gene transfer achieved in a variety of organ contexts.

Adenoviral particles may be used to advantage as vehicles for adequate gene delivery. Such virions possess a number of desirable features for such applications, including: structural features related to being a double stranded DNA nonenveloped virus and biological features such as a tropism for the human respiratory system and gastrointestinal tract. Moreover, adenoviruses are known to infect a wide variety of cell types in vivo and in vitro by receptor-mediated endocytosis. Attesting to the overall safety of adenoviral vectors, infection with adenovirus leads to a minimal disease state in humans comprising mild flu-like symptoms.

Due to their large size (~36 kilobases), adenoviral genomes are well suited for use as gene therapy vehicles because they can accommodate the insertion of foreign DNA following the removal of adenoviral genes essential for replication and nonessential regions. Such substitutions render the viral vector impaired with regard to replicative functions and infectivity. Of note, adenoviruses have been used as vectors for gene therapy and for expression of heterologous genes.

For a more detailed discussion of the use of adenovirus vectors utilized for gene therapy, see Berkner, 1988, Biotechniques 6:616-629 and Trapnell, 1993, Advanced Drug Delivery Reviews 12:185-199.

It is desirable to introduce a vector that can provide, for example, multiple copies of a desired gene and hence greater amounts of the product of that gene. Improved adenoviral vectors and methods for producing these vectors have been described in detail in a number of references, patents, and patent applications, including: Mitani and Kubo (2002, Curr Gene Ther, 2(2):135-44); Olmsted-Davis et al. (2002, Hum Gene Ther. 13(11):1337-47); Reynolds et al. (2001, Nat Biotechnol. 19(9):838-42); U.S. Pat. Nos. 5,998,205 (wherein tumor-specific replicating vectors comprising multiple DNA copies are provided); 6,228,646 (wherein helper-free, totally defective adenovirus vectors are described); 6,093,699 (wherein vectors and methods for gene therapy are provided); 6,100,242 (wherein a transgene-inserted replication defective adenovirus vector was used effectively in in vivo gene therapy of peripheral vascular disease and heart disease); and International Patent Application Nos. WO 94/17810 and WO 94/23744.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of the variant zymogen/proteases or functional fragments thereof. For example, an E1 deleted type 5 adenoviral vector comprising nucleic acid sequences encoding variant zymogen/protease under the control of a cytomegalovirus (CMV) promoter may be used to advantage in the methods of the present invention.

Exemplary Methods for Producing Adenoviral Vectors

Adenoviral vectors for recombinant gene expression have been produced in the human embryonic kidney cell line 293 (Graham et al., 1977, J. Gen. Virol. 36:59-72). This cell line is permissive for growth of adenovirus 2 (Ad2) and adenovirus 5 mutants defective in E1 functions because it comprises the left end of the adenovirus 5 genome and, therefore, expresses E1 proteins. E1 genes integrated into the cellular genome of 293 cells are expressed at levels which facilitate the use of these cells as an expression system in which to amplify viral vectors from which these genes have been deleted. 293 cells have been used extensively for the isolation and propagation of E1 mutants, for helper-independent cloning, and for expression of adenovirus vectors. Expression systems such as the 293 cell line, therefore, provide essential viral functions in trans and thereby enable propagation of viral vectors in which exogenous nucleic acid sequences have been substituted for E1 genes. See Young et al. in The Adenoviruses, Ginsberg, ed., Plenum Press, New York and London (1984), pp. 125-172.

Other expression systems well suited to the propagation of adenoviral vectors are known to those of skill in the art (e.g., HeLa cells) and have been reviewed elsewhere.

Also included in the present invention is a method for modulating hemostasis comprising providing cells of an individual with a nucleic acid delivery vehicle encoding a variant zymogen/protease polypeptide and allowing the cells to grow under conditions wherein the zymogen/protease polypeptide is expressed.

From the foregoing discussion, it can be seen that thrombin zymogen/protease polypeptides, and thrombin zymogen/protease polypeptide expressing vectors may be used in the treatment of disorders associated with aberrant blood coagulation.

C. Pharmaceutical Compositions

The expression vectors of the present invention may be incorporated into pharmaceutical compositions that may be delivered to a subject, so as to allow production of a biologically active protein (e.g., a variant zymogen/protease polypeptide or functional fragment or derivative thereof). In a particular embodiment of the present invention, pharmaceutical compositions comprising sufficient genetic material to enable a recipient to produce a therapeutically effective amount of a variant zymogen/protease polypeptide can influence hemostasis in the subject. Alternatively, as described above, pharmaceutical preparations comprising the thrombin polypeptide variant in a suitable biological buffer may be administered to a patient via intravenous bolus infusion. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents which influence hemostasis.

In preferred embodiments, the pharmaceutical compositions also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., 18th Edition, Easton, Pa. [1990]).

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art. The pharmaceutical compositions of the present invention may be manufactured in any manner known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they may be placed in an appropriate container and labeled for treatment. For administration of zymogen/protease-containing vectors, such labeling would include amount, frequency, and method of administration.

Pharmaceutical compositions suitable for use in the invention include compositions wherein the active ingredients are contained in an effective amount to achieve the intended therapeutic purpose. Determining a therapeutically effective dose is well within the capability of a skilled medical practitioner using the techniques and guidance provided above. Therapeutic doses will depend on, among other factors, the age and general condition of the subject, the severity of the aberrant blood coagulation phenotype, and the strength of the control sequences regulating the expression levels of the variant zymogen/protease polypeptide. Thus, a therapeutically effective amount in humans will fall in a relatively broad range that may be determined by a medical practitioner based on the response of an individual patient to vector-based zymogen/protease treatment.

D. Administration

Expression vectors of the present invention comprising nucleic acid sequences encoding variant zymogen/protease, or functional fragments thereof, or the variant thrombin polypeptides themselves may be administered to a patient by a variety of means (see below) to achieve and maintain a prophylactically and/or therapeutically effective level of the zymogen/protease polypeptide. One of skill in the art could readily determine specific protocols for using the zymogen/protease encoding expression vectors of the present invention for the therapeutic treatment of a particular patient. Protocols for the generation of adenoviral vectors and administration to patients have been described in U.S. Pat. Nos. 5,998,205; 6,228,646; 6,093,699; 6,100,242; and International Patent Application Nos. WO 94/17810 and WO 94123744, which are incorporated herein by reference in their entirety.

Variant zymogen/protease encoding adenoviral vectors of the present invention may be administered to a patient by any means known. Direct delivery of the pharmaceutical compositions in vivo may generally be accomplished via injection using a conventional syringe, although other delivery methods such as convection-enhanced delivery are envisioned (See e.g., U.S. Pat. No. 5,720,720). In this regard, the compositions may be delivered subcutaneously, epidermally, intradermally, intrathecally, intraorbitally, intramucosally, intraperitoneally, intravenously, intraarterially, orally, intrahepatically or intramuscularly. Other modes of administration include oral and pulmonary administration, suppositories, and transdermal applications. A clinician specializing in the treatment of patients with blood coagulation disorders may determine the optimal route for administration of the adenoviral vectors comprising zymogen/protease nucleic acid sequences based on a number of criteria, including, but not limited to: the condition of the patient and the purpose of the treatment (e.g., enhanced or reduced blood coagulation).

The present invention also encompasses AAV vectors comprising a nucleic acid sequence encoding a variant zymogen/protease polypeptide.

Also provided are lentivirus or pseudo-typed lentivirus vectors comprising a nucleic acid sequence encoding a variant zymogen/protease polypeptide.

Also encompassed are naked plasmid or expression vectors comprising a nucleic acid sequence encoding a variant zymogen/protease polypeptide.

Intravenous bolus infusion of the variant thrombin polypeptide in a biologically acceptable carrier provides a particularly preferred embodiment of the invention.

The following example is provided to illustrate certain embodiments of the invention. It is not intended to limit the invention in any way.

EXAMPLE 1

Variant Thrombin Zymogen Protease

Prothrombinase catalyzes thrombin formation by the ordered cleavage of two peptide bonds in prothrombin. Although these bonds are likely 36 Å apart, sequential cleavage of prothrombin at Arg-320 to produce meizothrombin, followed by its cleavage at Arg-271, are both accomplished by equivalent exosite interactions that tether each substrate to the enzyme and facilitate presentation of the scissile bond to the active site of the catalyst. We show that impairing the conformational transition from zymogen to active proteinase that accompanies the formation of meizothrombin has no effect on initial cleavage at Arg-320 but inhibits subsequent cleavage at Arg-271. Full thermodynamic rescue of this defective mutant was achieved by stabilizing the proteinase-like conformation of the intermediate with a reversible, active site specific inhibitor. Irreversible stabilization of intact prothrombin in a proteinase-like state, even without prior cleavage at Arg-320, also enhanced cleavage at Arg-271. Our results indicate that the sequential presentation and cleavage of the two scissile bonds in prothrombin activation is accomplished by substrate bound either in the zymogen or proteinase conformations. The ordered cleavage of prothrombin by prothrombinase is driven by ratcheting of the substrate from the zymogen to the proteinase-like states.

Materials and Methods

Reagents.

The inhibitors D-phenylalanyl-L-prolyl-L-arginine chloromethylketone (FPR-CH$_2$Cl, Calbiochem) and dansyl-L-arginine N-(3-ethyl-1,5-pentanediyl)amide (DAPA, HematologicTechnologies, Essex, Vt.) were obtained from the indicated sources. The peptidyl substrate, H-D-phenylalanyl-L-pipecolyl-L-arginine-P-nitroanilide (S2238), was from Chromogenix. Small unilamellar phospholipid vesicles (PCPS) composed of 75% (WT WT) hen egg L-α-phosphatidylcholine and 25% (WT WT) porcine brain L-α-phosphatidylserine (Avanti Polar Lipids) were prepared and characterized as described in ref. 15. Factors Xa and Va were prepared from factors X and V purified from human plasma and quality controlled as described in refs. 3, 4, and 16. A fragment comprising residues 1-325 of staphylocoagulase containing an additional Met at the NH$_2$ terminus and a His tag at fused to the COOH terminus (Met-SC$_{1-325}$-His-6) was prepared by modification of an expression construct described in ref. 13. Deletion of a stop codon allowed translation of an additional Lys-Leu-Ala-Ala-Ala-Leu-Glu-His-6 (SEQ ID NO: 3) sequence at the COOH terminus. Met-SC$_{1-325}$-His-6 was expressed as described in ref. 13 and purified by affinity chromatography by using Ni$^{2+}$-iminodiacetic acid Sepharose (Amersham Pharmacia). Unless otherwise stated, kinetic studies were performed in 20 mM Hepes/0.15 M NaCl/5 mM Ca$^{2+}$/0.1% (wt/vol) PEG 8000, pH 7.4 (assay buffer) at 25° C. Extinction coefficients ($E_{280}$ mg$^{-1}$·cm$^2$) and molecular weights ($M_r$) used to determine protein concentrations were Xa: 1.16, 45,300 (17); Va: 1.78, 173,000 (18); Met-SC$_{1-325}$-His-6: 1.00, 38,000; and all recombinant prothrombin variants: 1.47, 72,000 (4).

Recombinant Prothrombin Variants.

Procedures for the expression and characterization of recombinant wild-type human II (II$_{WT}$) and II containing Gln in place of Arg-320 (II$_{Q320}$), have been described in ref. 4. The cDNA encoding human II was used as a template for mutagenesis by using the QuikChange mutagenesis kit (Stratagene) to replace codons encoding Ile-321-Val-322-Glu-323 with codons for Thr-Ala-Thr (II$_{TAT}$, II containing Thr-Ala-Thr after Arg-320) and to replace codons for Arg-155 and Arg-284 with codons for Gln (II$_{Q155,284}$, thrombin-resistant variant of II containing Gln in place of Arg-155 and Arg-284). The Gateway system (Invitrogen) was used to transfer the cassette encoding the prothrombin variants to an adapted pCDNA 3.1 (+) vector as described in ref. 4, and the integrity of each cassette was established by DNA sequencing. Transfection of HEK293 cells, selection of stable cell lines, large-scale expression, and purification of II$_{TAT}$ and II$_{Q155,Q284}$ were performed as described in ref. 4. NH$_2$-terminal sequencing and quantitative determination of γ-carboxyglutamic acid content, as described in refs. 4 and 19, established a correctly processed NH2-terminal sequence and a full complement of γ-carboxyglutamic acid residues for each prothrombin variant (data not shown).

Preparation of FPR-II$_{Q320}$.

Conformational activation of II$_{Q320}$ and its covalent inactivation with FPR-CH$_2$Cl was accomplished by the addition of 43 µM Met-SC$_{1-325}$-His-6 to a reaction mixture equilibrated at 25° C. containing 25 µM II$_{Q320}$ and 250 µM FPR-CH$_2$Cl in 140 mM Hepes/76 mM NaCl/11% (vol/vol) glycerol, pH 7.8. Conformationally activated II$_{Q320}$ was 99% inhibited after 10 min, as measured by initial rates of S2238 hydrolysis. The incubation was continued for an additional 75 min, and the Met-SC$_{1-325}$-His-6 FPR-II$_{Q320}$ complex was captured by application to a column of Ni$^{2+}$-iminodiacetic acid-Sepharose equilibrated in 50 mM Hepes/400 mM NaCl/50 mM imidazole/10 µM FPR-CH$_2$Cl, pH 7.4. II$_{Q320}$ covalently modified with FPR-CH$_2$Cl after conformational activation (FPPII$_{Q320}$) was eluted with 50 mM Hepes/125 mM NaCl/3 M NaSCN, pH 7.4, dialyzed against 50 mM Hepes 125 mM NaCl, pH 7.4, and separated from trace amounts of Met-SC$_{1-325}$-His-6 FPR-II$_{Q320}$ complex by chromatography on tandem Superdex 200 HR 10 30 columns (Amersham Pharmacia) equilibrated in the same buffer. FPR- $II_{Q320}$ free of Met-$SC_{1-325}$-His-6, eluting in the second of two peaks, was pooled, snap-frozen, and stored at 70° C. Residual uninhibited $II_{Q320}$ was estimated at 0.5%, as determined from the rate of S2238 hydrolysis after incubation of 100 nM FPR-$II_{Q320}$ with a staphylocoagulase fragment comprising residues 1-325 (250 nM) for 20 min at 25° C. A control substrate was prepared by treating $II_{Q320}$ with 3 M NaSCN for 2 h at room temperature, followed by gel filtration into 50 mM Hepes/0.11 M NaCl 15 mM $Ca^{2+}$/0.1% (wt/vol) PEG 8000, pH 7.4 and dialysis into 50 mM Hepes/125 mM NaCl, pH 7.4 before freezing. Both $II_{Q320}$ and FPR-$II_{Q320}$ were thawed and diluted into 35 mM Hepes/0.15 M NaCl/2 mM $Ca^{2+}$/0.1% (wt/vol) PEG 8000, pH 7.4 before use.

Kinetics of Bond Cleavage in Prothrombin Variants.

Reaction mixtures prepared in assay buffer and maintained at 25° C., contained 5.4 µM $II_{WT}$, $II_{TAT}$, or $II_{Q155,Q284}$, 20 µM POPS, 28 nM Va, and indicated concentrations of DAPA. Cleavage was initiated by the addition of 0.8 nM Xa and samples (15 µl), withdrawn at the indicated times, were quenched by mixing with an equal volume of 2 NuPAGE LDS sample buffer (Invitrogen) containing 50 mM EDTA. Quenched samples were treated with 71 mM DTT, heated at 89° C. for 5 min, and subjected to electrophoresis (4.2 µg protein per lane) by using NuPAGE 4-12% gels and Mes running buffer (Invitrogen). Protein bands visualized by staining with Coomassie brilliant blue R-250 were imaged and analyzed by quantitative densitometry by using procedures described in detail in refs. 4 and 15. Analysis of the cleavage of FPR-$II_{Q320}$ and NaSCN-treated $II_{Q320}$ was performed as described above except that reaction mixtures contained 5.8 µM prothrombin variant, 50 µM PCPS, 60 nM Va, 40 µM DAPA, and 1 nM Xa. In all cases, representative findings are presented from two or more experiments performed at a comparable level of detail.

Binding of DAPA to Thrombin Variants.

Front face fluorescence measurements were performed in a plate reader (SpectraMax Gemini, Molecular Devices) by using black polystyrene plates (no. 3650, Corning). Reaction mixtures (100 µl) prepared in assay buffer contained increasing concentrations of DAPA (24 concentrations, 0-100 µM) with no addition, 0.5 µM IIa, or 0.5 µM $IIa_{TAT}$. Fluorescence intensity was determined by integrating emission spectra between 510 and 530 nm at 25° C. by using $\lambda$EX 280 nm with a 495-nm long-pass filter in the emission beam. Subtraction of the intensity measured with DAPA alone yielded the fluorescence change associated with the binding of DAPA to IIa or $IIa_{TAT}$. Fluorescence data were analyzed as described in ref. 7 to infer the equilibrium dissociation constant.

Results

Activation-Defective Variant of Prothrombin. Initial cleavage of prothrombin at Arg-320 reveals a new $NH_2$-terminal sequence (Ile-Val-Glu) that is essential for the formation of an internal salt bridge. Salt bridge formation induces conformational changes in the proteinase domain and maturation of the active serine proteinase (11, 13, 20). We prepared a recombinant prothrombin derivative ($II_{TAT}$) in which the Ile-Val-Glu sequence was replaced with Thr-Ala-Thr, normally found after the Arg-271 cleavage site. The intent was to produce a prothrombin variant that could be cleaved normally but with impaired ability to undergo the conformational transition to active proteinase after cleavage at Arg-320. Accordingly, $II_{TAT}$ could be fully converted to $IIa_{TAT}$ after prolonged digestion with prothrombinase (see below). Although correct cleavage at Arg-320 was verified by $NH_2$-terminal sequencing, purified $IIa_{TAT}$ exhibited only 0.2% of the specific activity of wild-type IIa as determined by initial velocity measurements with 100 µM S2238 (data not shown).

Kinetics of Prothrombin Cleavage.

Cleavage of $II_{WT}$ by prothrombinase yielded bands established to arise from the sequential cleavage at Arg-320, yielding mIIa as the sole intermediate, followed by cleavage at Arg-271 to produce IIa (4). Prothrombin disappearance was accompanied by the transient appearance of F1.2-A, uniquely associated with mIIa formation, followed by the delayed appearance of F1.2 and A chain of IIa denoting IIa production (FIG. 1A), Cleavage of $II_{WT}$ has been established to be qualitatively and quantitatively indistinguishable from the cleavage of prothrombin isolated from plasma (4). An equivalent banding pattern and key diagnostic features of the reaction profile observed with $II_{TAT}$ (FIG. 1B) implicated the same order of bond cleavage in this variant. However, although $II_{TAT}$ disappeared in a way that was comparable with $II_{WT}$, the band arising from $mIIa_{TAT}$ produced after initial cleavage at Arg-320 was more intense and persisted throughout the time course. Bands arising from $IIa_{TAT}$ produced by the second cleavage reaction at Arg-271 appeared more slowly (FIG. 1B).

Figure 2A:
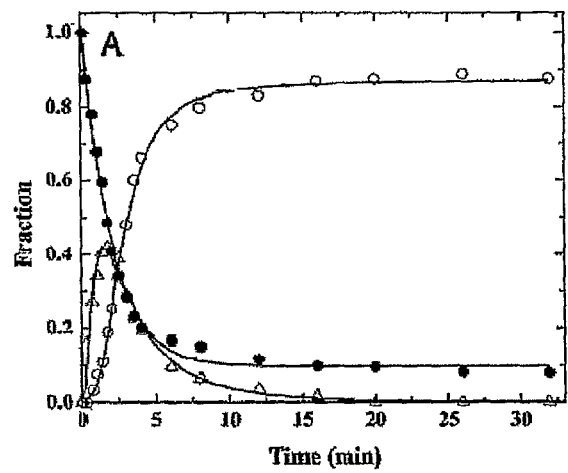
FIG. 2. Reaction profiles for the action of prothrombinase on $II_{WT}$ and $II_{TAT}$. Progress curves for reactants and products in the activation of $II_{WT}$ with 60 μM DAPA (A) or $II_{TAT}$ in the absence of DAPA (B) were obtained by quantitative densitometry. Curves illustrate the disappearance of II (●), the transient formation of mIIa (△), and the accumulation of IIa (○). The lines were arbitrarily drawn.
Figure 2B:
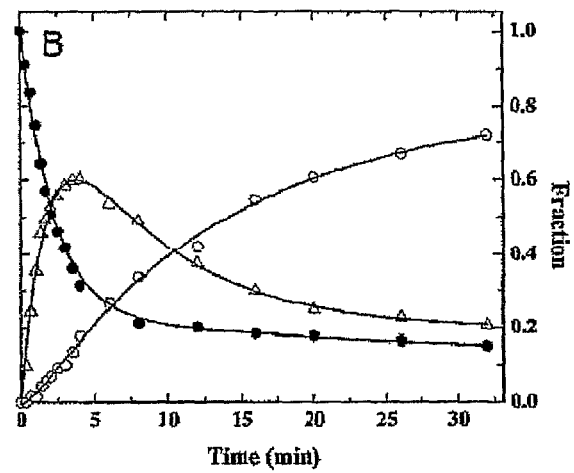

Quantitative densitometry yielded a reaction profile for $II_{WT}$ cleavage that was consistent with the sequential conversion of $II_{WT}$ to mIIa, followed by its cleavage at Arg-271, to produce IIa (FIG. 2A). Initial rates of consumption of $II_{WT}$ and $II_{TAT}$, resulting from cleavage at Arg-320, were comparable and differed only by 15% (FIG. 2). The lower extent of $II_{TAT}$ consumption most likely reflects the results of product inhibition by the accumulating intermediate. For either substrate, mIIa was produced at the same initial rate. However, $mIIa_{TAT}$ accumulated to a greater extent and decayed slowly, with significant amounts evident even after 30 min, whereas $IIa_{TAT}$ was produced at a slower rate (FIG. 2B). Additional data points extending to 120 min established quantitative conversion of $II_{TAT}$ to $IIa_{TAT}$ (data not shown).

Figure 3:
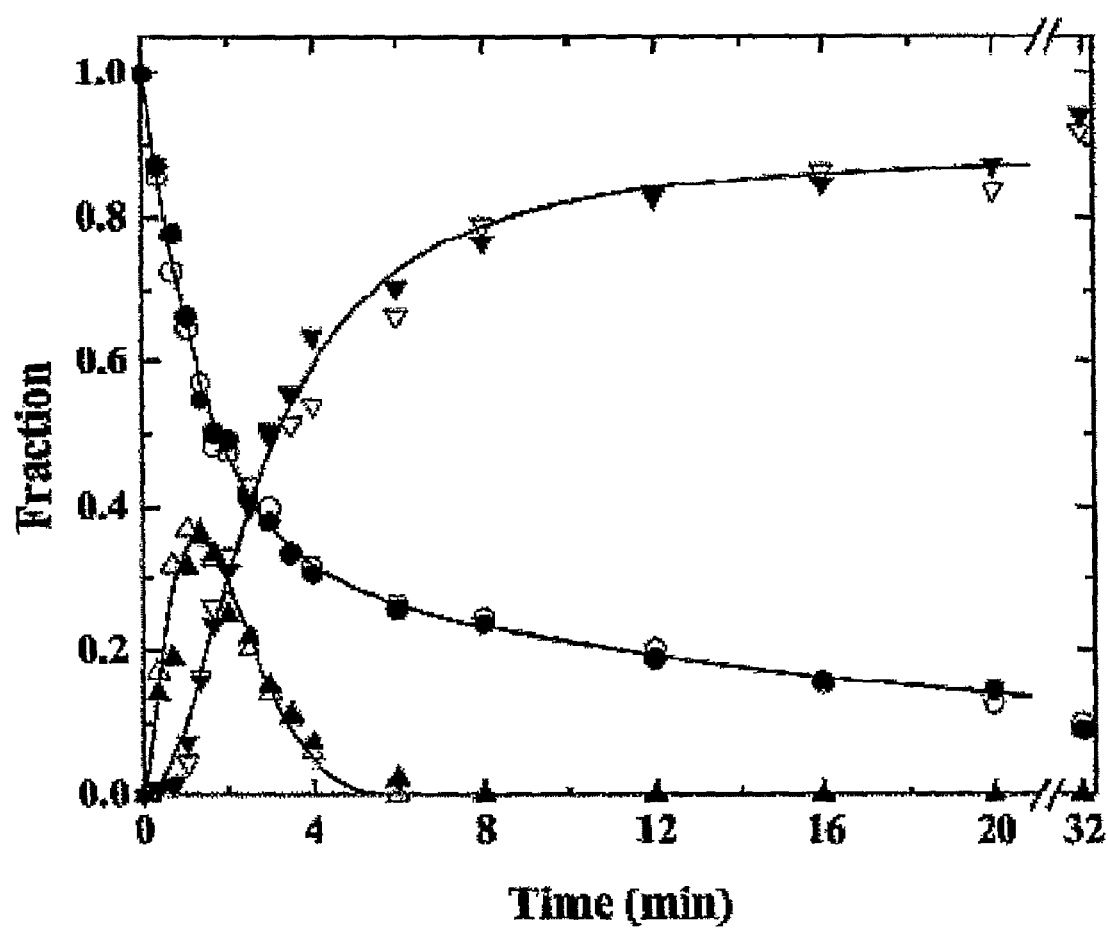
FIG. 3. Effect of DAPA on the cleavage of $II_{Q155,Q284}$. SDS PAGE and quantitative densitometry for the activation of $II_{Q155,Q284}$ (5.4 μM) with 0.8 nM prothrombinase (0.8 nM Xa/31 nM/Va 20 μM PCPS) in the absence of DAPA (open symbols) or in the presence of 60 μM DAPA (filled symbols). The disappearance of II (○ and ●), the transient formation of mIIa (△ and ▲) and the accumulation of IIa (∇ and ▼) are illustrated. The lines were arbitrarily drawn.

Studies of $II_{WT}$ cleavage require the use of DAPA, a tight binding inhibitor of IIa and mIIa, to prevent feedback cleavages in the substrate and intermediate (FIGS. 1A and 2A). DAPA was not present in studies with $II_{TAT}$ (FIGS. 1B and 2B). Differences in the cleavage of $II_{WT}$ and $II_{TAT}$ could reflect an unexpected effect of DAPA unrelated to the sequence after the Arg-320 cleavage site. This possibility was eliminated by the results of studies with and without DAPA by using $II_{Q155,Q284}$, a thrombin resistant variant (FIG. 3). The reaction profile for $II_{Q155,Q284}$ cleavage by prothrombinase was comparable with that observed for the cleavage of $II_{WT}$ both in the presence and absence of 60 µM DAPA (FIG. 3).

The data indicate that mutation of the residues after the Arg-320 cleavage site and the associated impairment in proteinase formation has minimal impact on the first cleavage reaction at Arg-320 but produces a distant effect on subsequent cleavage at Arg-271. Integration of the area under the progress curve for mIIa formation (extending to 120 min) suggests that the second cleavage reaction is 20-fold slower in $II_{TAT}$ than in $II_{WT}$ or in $II_{Q155,Q284}$.

Rescue of $II_{TAT}$ Cleavage by DAPA.

Figure 4:
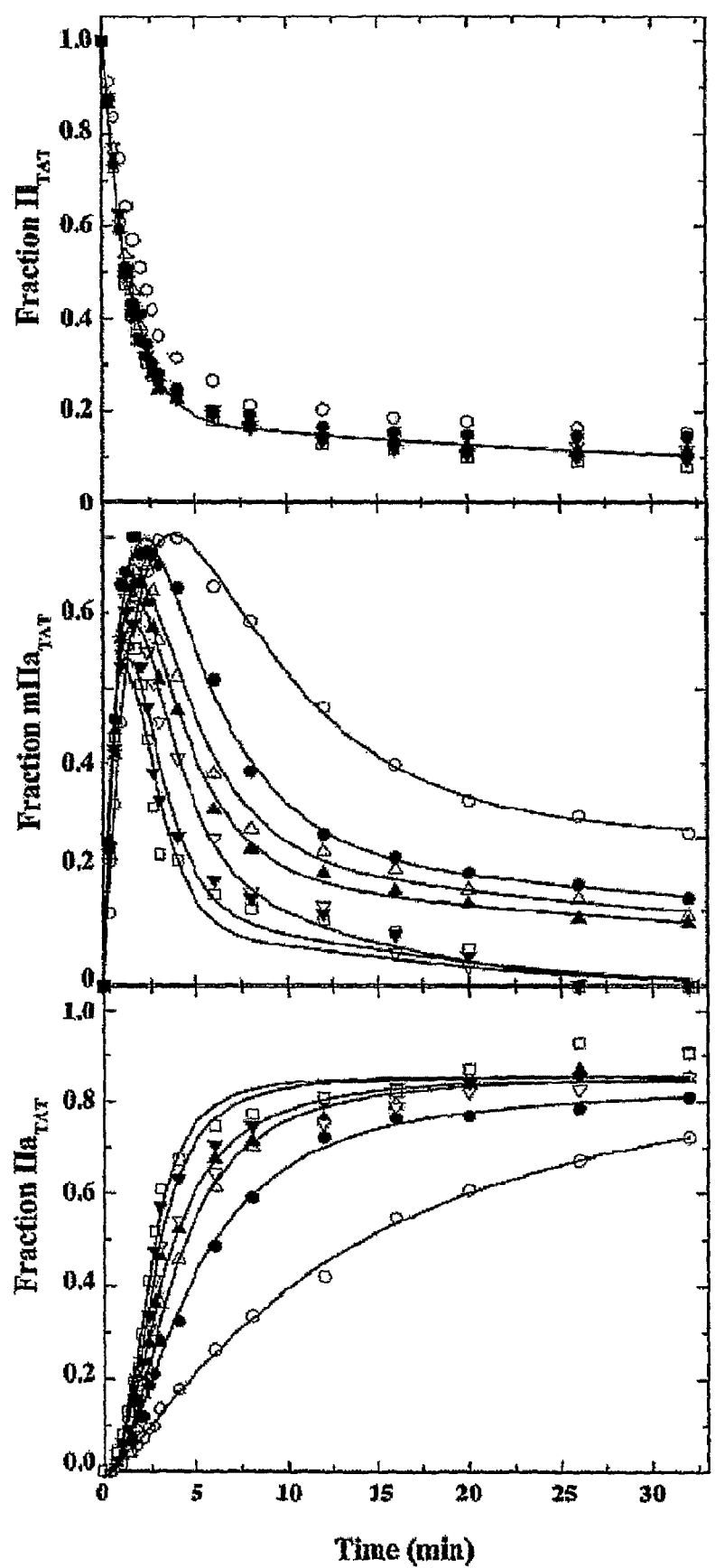
FIG. 4. Modulation of $II_{TAT}$ cleavage by DAPA. $II_{TAT}$ (5.4 μM) was activated by 0.8 nM prothrombinase (0.8 nM Xa/28 nM Va/20 μM PCPS) in the presence of 0 (○), 20 μM (●), 40 μM (△), 60 μM (▲), 100 μM (∇), 200 μM (▼) and 300 μM (□) DAPA. Progress curves, obtained by SDS PAGE and quantitative densitometry, illustrate the fates of $II_{TAT}$ (Top), $mIIa_{TAT}$ (Middle), and $IIa_{TAT}$ (Bottom). Additional data points extending to 120 min have been omitted for clarity. All lines were arbitrarily drawn.

In contrast to the findings with $II_{Q155,Q284}$, DAPA significantly altered product profiles of $II_{TAT}$ cleavage without detectably influencing bond cleavage order. DAPA had a minor effect on $II_{TAT}$ consumption (FIG. 4). Increasing concentrations of DAPA, as high as 300 µM, did not significantly affect the initial rate of $mIIa_{TAT}$ formation but decreased the amplitude of $mIIa_{TAT}$ production and increased the rate of $IIa_{TAT}$ formation (FIG. 4). At saturating concentrations of DAPA, progress curves for $mIIa_{TAT}$ and $IIa_{TAT}$ resembled those obtained in the activation of $II_{WT}$. The observations indicate that DAPA has a minimal effect on the initial cleavage of $II_{TAT}$ at Arg-320 but can rescue defective cleavage at Arg-271. This rate-enhancing effect of DAPA on Arg-271 cleavage is specific to the action of prothrombinase on $II_{TAT}$.

Figure 5:
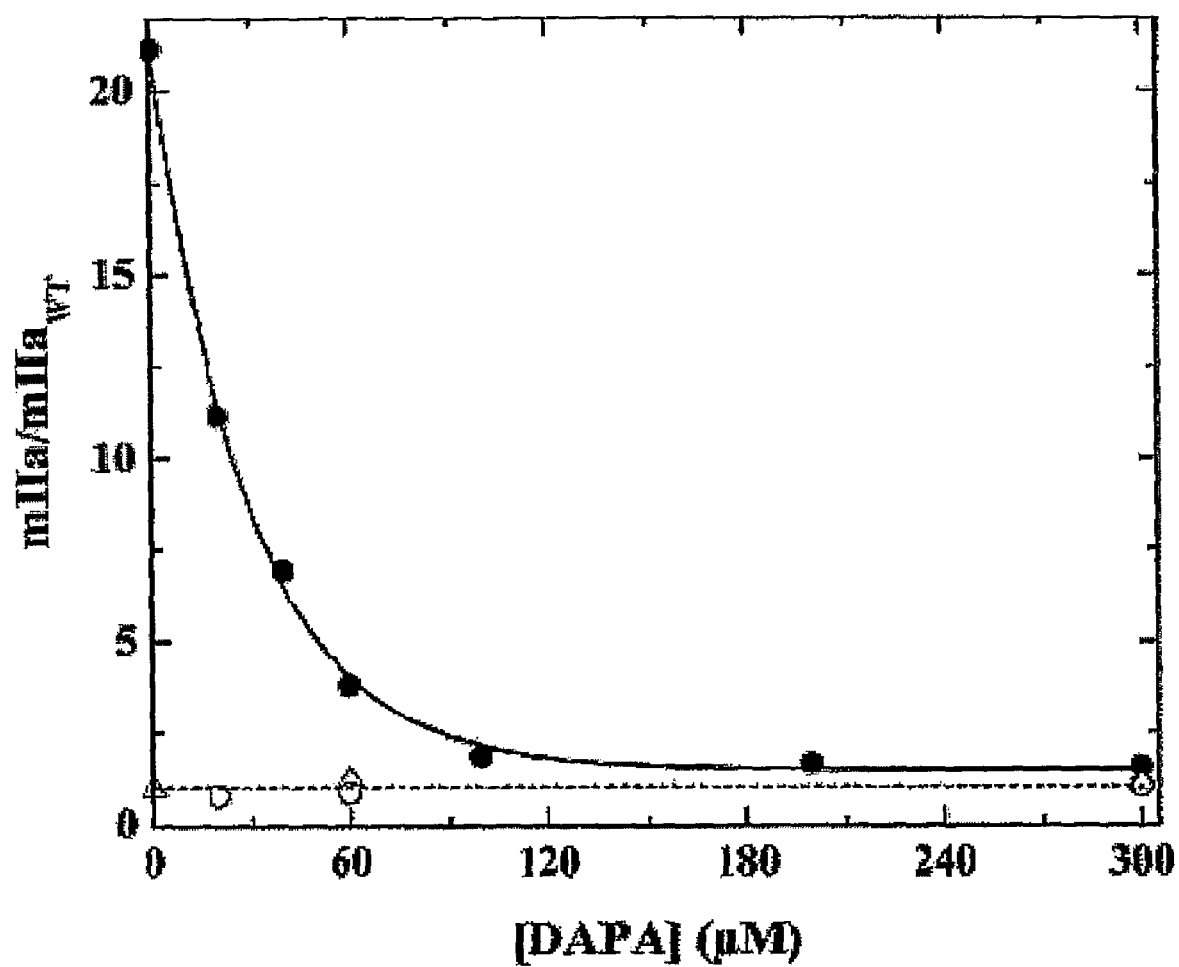
FIG. 5. Effect of DAPA on meizothrombin accumulation. Total meizothrombin accumulation in the cleavage of $II_{WT}$ (○), $II_{TAT}$ (○), and $II_{Q155,Q284}$ (△) as a function of increasing concentrations of DAPA was estimated by integrating areas under progress curves and normalizing the value to the area under the mIIa progress curve with $II_{WT}$ measured at 60 μM DAPA. The dashed line denotes a value of 1. The solid line was arbitrarily drawn.

Effects of DAPA were assessed by integrating areas under the progress curves for mIIa formation and its disappearance for the different prothrombin variants (FIG. 5). Normalized areas obtained in the activation of $II_{WT}$ or $II_{Q155,Q284}$ were identical and were independent of DAPA varied between 0 and 300 μM for $II_{Q155,Q284}$ or 20 and 300 μM for $II_{WT}$. In the case of $II_{TAT}$, the integrated area (obtained by integration to 120 min) was 20-fold higher in the absence of DAPA and decreased saturably to values observed with $II_{WT}$ (FIG. 5). Thus, a defective second half-reaction in $II_{TAT}$ cleavage is fully rectified by high concentrations of DAPA with a half-maximal effect at ≈20 μM.

Although DAPA is established to act as a tight-binding, active site-directed inhibitor of IIa and mIIa (Kd≈1 nM) (21), the data imply a far weaker interaction between DAPA and $mIIa_{TAT}$ or $IIa_{TAT}$. Fluorescence studies assessing the binding of DAPA to $IIa_{WT}$ were consistent with a nanomolar equilibrium dissociation constant (data not shown). Although the amplitude of the fluorescence change observed with $IIa_{TAT}$ and saturating concentrations of DAPA was comparable with that observed with $IIa_{TAT}$, DAPA bound weakly to purified $IIa_{TAT}$ with Kd=31.7±2.3 M (data not shown). This dissociation constant is in agreement with the concentration of DAPA required to observe 50% rescue of $II_{TAT}$ cleavage (FIG. 5).

One interpretation of the results is that the full rescue of Arg-271 cleavage in $II_{TAT}$ by high concentrations of DAPA arises from its weak interaction with $mIIa_{TAT}$ and the thermodynamic stabilization of a proteinase-like state in an otherwise zymogen-like $mIIa_{TAT}$ species produced after the initial cleavage at Arg-320. This interpretation implies that effective presentation of structures flanking the Arg-271 site to the active site of prothrombinase requires a substrate in a proteinase-like configuration.

Stabilization of the Uncleaved Zymogen in a Proteinase-Like State.

Figure 6:
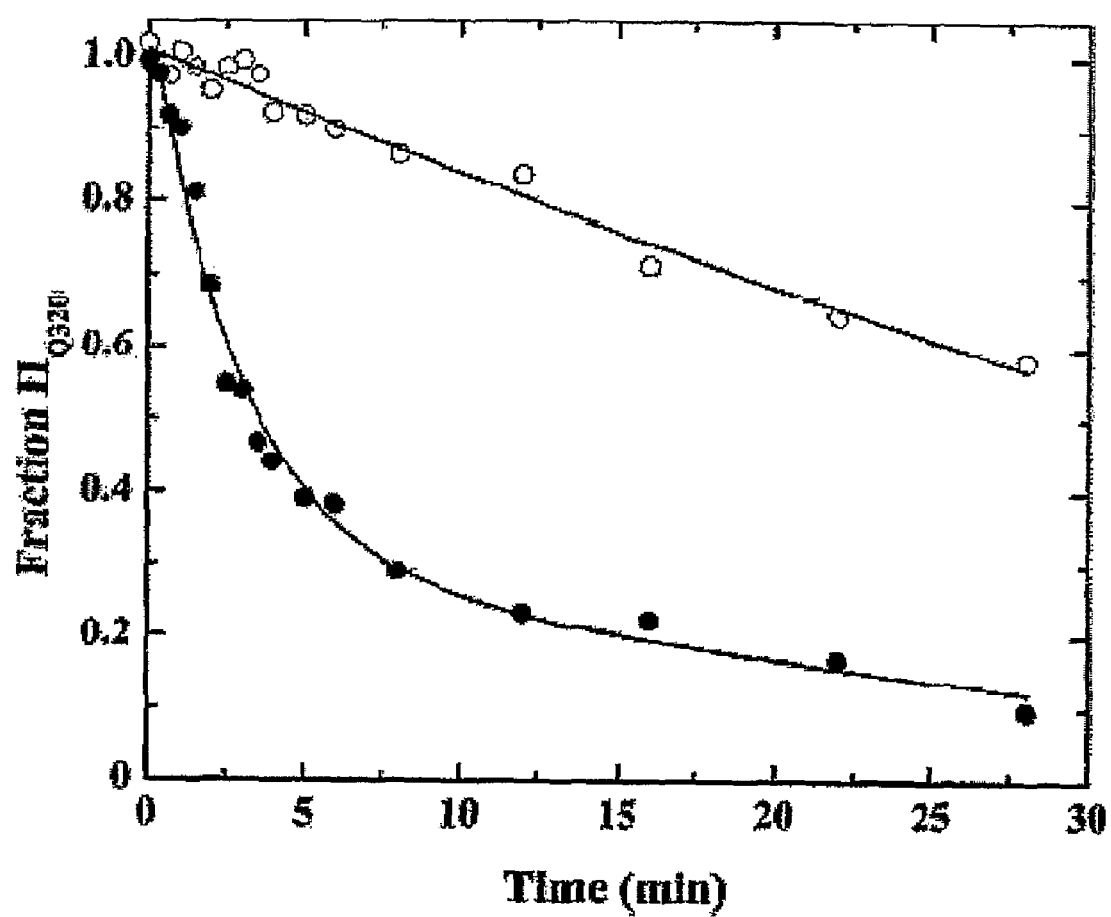
FIG. 6. Cleavage at Arg-271 in the uncleaved zymogen. Prothrombin derivatives (5.8 μM) were digested with 1 nM prothrombinase (1 nM Xa/60 nM Va/50 μM PCPS) in the presence of 40 μM DAPA. The fraction of $II_{Q320}$ (○) and FPR-$II_{Q320}$ (●) remaining as a function of time was determined by SDS PAGE and quantitative densitometry. The lines were arbitrarily drawn.

Prior work with a prothrombin variant ($II_{Q320}$) containing a single cleavable site at Arg-271 has established that the Arg-271 site in the intact zymogen is cleaved slowly by prothrombinase (4). In agreement, analysis by SDS PAGE and quantitative densitometry showed slow cleavage at Arg-271 in $II_{Q320}$ (FIG. 6). FPR-$II_{Q320}$ was produced by conformational activation of $II_{Q320}$ with Met-$SC_{1-325}$-His-6, covalent inactivation of the complex with FPR-$CH_2Cl$, followed by dissociation and separation from Met-$SC_{1-325}$-His-6. FPR-$II_{Q320}$ is an uncleaved prothrombin analog that is expected to be stabilized in a more proteinase-like state by the inhibitor covalently bound to the active site. Cleavage at Arg-271 in FPR-$II_{Q320}$ by prothrombinase was enhanced 12-fold in comparison with cleavage at the same site in $II_{Q320}$ (FIG. 6). Thus, stabilization of the substrate in a proteinase-like state, even without cleavage at Arg-320, enhances presentation and cleavage at Arg-271.

Discussion

Figure 7:
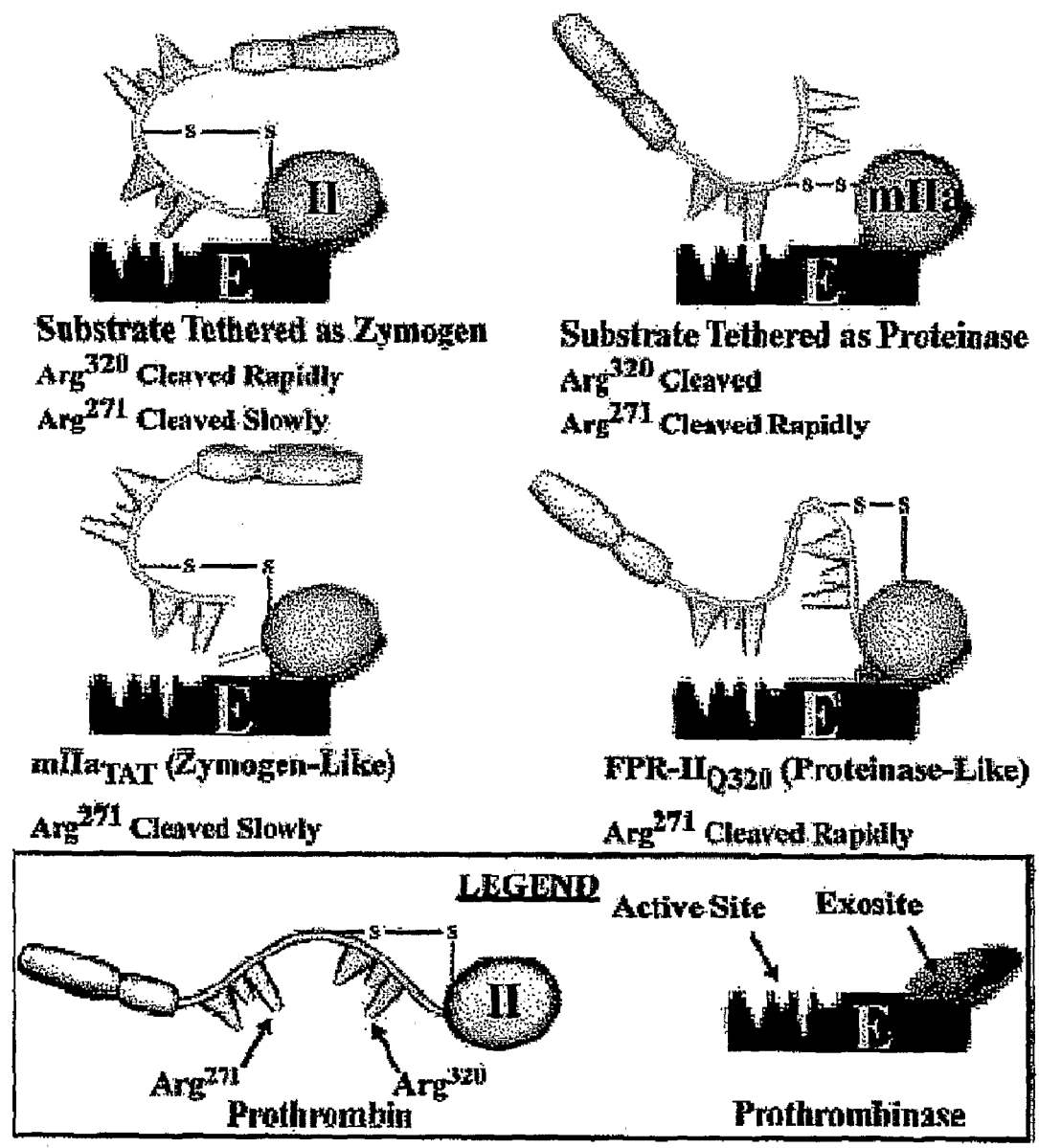
FIG. 7. Substrate bound to prothrombinase in either the zymogen or proteinase configurations. Substrate species in either the zymogen or proteinase states are illustrated to be bound to prothrombinase through exosite interactions. For clarity, only the different forms of such possible enzyme-substrate complexes are illustrated without additional steps reflecting substrate binding or intermediate dissociation.

Our observations, along with the mechanisms established for substrate recognition by prothrombinase (8), are consistent with the interpretations outlined in FIG. 7. Exosite-dependent tethering of the substrate to prothrombinase in either the zymogen or the proteinase configurations is proposed to govern presentation of the individual cleavage sites for docking to the active site of the catalyst and cleavage (FIG. 7). Active site docking of the Arg-320 site is facilitated when the substrate is bound in the zymogen configuration, whereas effective presentation of the Arg-271 site requires that the substrate is bound in the proteinase configuration after initial cleavage at Arg-320. These ideas provide an explanation, at the molecular level, for bond selectivity and the largely ordered action of prothrombinase on the two spatially distinct cleavage sites in prothrombin.

Selective impairment of the second cleavage reaction in the activation of $II_{TAT}$ is proposed to reflect the suboptimal presentation of the Arg-271 site because of the zymogen-like configuration of $mIIa_{TAT}$ despite its prior cleavage at Arg-320 (FIG. 7). Conversely, forcing the zymogen to adopt a proteinase-like configuration yields enhanced presentation and cleavage at Arg-271 even without prior cleavage at Arg-320 (FIG. 7). Thus, the conformational transition of the substrate between zymogen and proteinase states plays a role in regulating the action of prothrombinase on the two cleavage sites in the protein substrate.

The structural basis for the conversion of zymogen to proteinase in the chymotrypsin-like serine proteinases fold has been established with numerous x-ray structures, including those for derivatives of II, mIIa, and IIa (10-14, 22). The Ile-Val-Glu $NH_2$ terminus generated after cleavage at Arg-320 inserts into the $NH_2$-terminal binding cleft in the catalytic domain and yields a salt bridge between Ile-321 (IleC16) and AspC194 (Residues in the proteinase domain, numbered according to the homologous residues in chymotrypsinogen (22)), are denoted by a C preceding the residue number). Salt bridge formation triggers conformational changes in the putative activation domains (11-14, 23, 24). These changes are associated with the formation of the substrate binding pocket and the oxyanion hole required for catalysis (11-14, 22). In the case of mIIa, these conformational changes could also be transmitted to the other domains that remain covalently attached (25). Because formation of the internal salt bridge depends on the $NH_2$-terminal sequence produced after cleavage at Arg-320, some or all of these linked changes are likely disrupted in $mIIa_{TAT}$ (11, 24). It is not possible to discern whether impaired cleavage at Arg-271 in $mIIa_{TAT}$, which we have ascribed to its zymogen-like nature, arises from all or a subset of the linked conformational changes associated with the zymogen to proteinase transition.

Full and specific rescue of the defect in $II_{TAT}$ cleavage by high concentrations of DAPA indicates that this active site-directed ligand somehow rectifies impaired docking of the Arg-271 cleavage site with the active site of prothrombinase in the otherwise zymogen-like $mIIa_{TAT}$ (FIG. 7). Ligands that bind with high affinity to the proteinase are established to enhance the ability of the zymogen to adopt a proteinase-like-configuration (13, 20, 23). Our findings are consistent with two possible interpretations DAPA could bind weakly (Kd 30 μM) to the zymogen-like $mIIa_{TAT}$ and overcome a kinetic and or thermodynamic barrier in its conversion to the proteinase-like state. Alternatively, DAPA could act by selectively binding and favoring the proteinase in an equilibrium between zymogen-like and proteinase-like forms of $mIIa_{TAT}$ in which the zymogen-like state is highly favored.

Effectively ordered cleavage of prothrombin by prothrombinase arises because Arg-271 in intact prothrombin is cleaved with a $V_{max}$ that is ≈30-fold lower than for cleavage at Arg-320, and prior cleavage at Arg-320 increases the $V_{max}$ for cleavage at Arg-271 by a factor of ≈30 (4). Provided the ideas outlined in FIG. 7 can fully explain the differential recognition of the two sites in prothrombin, blocking the conformational transition to proteinase is expected to maximally yield a 30-fold slower rate of cleavage at Arg-271, even after cleavage at Arg-320. Complete stabilization of the zymogen in the proteinase state is expected to maximally yield a ≈30-fold enhancement in cleavage at Arg-271, even without prior cleavage at Arg-320. These boundary conditions, established by the kinetic constants measured for the individual cleavage reactions, are generally consistent with the magnitude of effects we have observed. The somewhat smaller enhancement (≈12-fold) observed in Arg-271 cleavage in FPR-II$_{Q320}$ could reflect the possibility that this derivative has not been completely driven to a proteinase-like state. Nevertheless, taken together, the results illustrate that it is not cleavage at Arg-320 per se but the ensuing conformational change that facilitates subsequent cleavage at Arg-271.

Our findings now provide a comprehensive explanation for a range of kinetic findings and an explanation for how ordered cleavage of prothrombin is achieved. Ratcheting of the substrate from the zymogen to proteinase conformations drives the sequential presentation of the two cleavage sites to the active site of the catalyst leading to the ordered action of prothrombinase on prothrombin. These concepts may also have bearing on the mechanisms underlying the ordered action of proteinases at multiple sites in their protein substrates in coagulation and in other areas of biology.

REFERENCES FOR EXAMPLE 1

1. Mann, K. G., Jenny, R. J. & Krishnaswamy, S. (1988) Annu. Rev. Biochem. 57, 915-956.
2. Mann, K. G., Nesheim, M. E., Church, W. R., Haley, P. & Krishnaswamy, S. (1990) Blood 76, 1-16.
3. Krishnaswamy, S., Church, W. R., Nesheim, M. E. & Mann, K. G. (1987) J. Biol. Chem. 262, 3291-3299.
4. Orcutt, S. J. & Krishnaswamy, S. (2004) J. Biol. Chem. 279, 54927-54936.
5. Esmon, C. T., Owen, W. G. & Jackson, C. M. (1974) J. Biol. Chem. 249, 606-611.
6. Carlisle, T. L., Bock, P. E. & Jackson, C. M. (1990) J. Biol. Chem. 265, 22044-22055.
7. Boskovic, D. S., Troxler, T. & Krishnaswamy, S. (2004) J. Biol. Chem. 279, 20786-20793.
8. Krishnaswamy, S. (2005) J. Thromb. Haemost. 3, 54-67.
9. Boskovic, D. S. & Krishnaswamy, S. (2000) J. Biol. Chem. 275, 38561-38570.
10. Martin, P. D., Malkowski, M. G., Box, J., Esmon, C. T. & Edwards, B. F. (1997) Structure (London) 5, 1681-1693.
11. Huber, R. & Bode, W. (1978) Acc. Chem. Res. 11, 114-122.
12. Khan, A, R. & James, M. N. G. (1998) Protein Sci. 7, 815-836.
13. Friedrich, I., Panizzi, P., Fuentes-Prior, P., Richter, K., Verhamme, I., Anderson, P. J., Kawabata, S., Huber, R., Bode, W. & Bock, P. E. (2003) Nature 425, 535-539.
14. Vijayalakshmi, J., Padmanabhan, K. P., Mann, K. G. & Tulinsky, A. (1994) Protein Sci. 3, 2254-2271.
15. Walker, R. K. & Krishnaswamy, S. (1994) J. Biol. Chem. 269, 27441-27450.
16. Buddai, S. K., Toulokhonova, L., Bergum, P. W., Vlasuk, G. P. & Krishnaswamy, S. (2002) J. Biol. Chem. 277, 26689-26698.
17. Di Scipio, R. G., Hermodson, M. A. & Davie, E. W. (1977) Biochemistry 16, 5253-5260.
18. Toso, R. & Camire, R. M. (2004) J. Biol. Chem. 279, 21643-21650.
19. Camire, R. M., Larson, P. J., Stafford, D. W. & High, K. A. (2000) Biochemistry 39, 14322-14329.
20. Bode, W. (1979) J. Mol. Biol. 127, 357-374.
21. Hibbard, L. S., Nesheim, M. E. & Mann, K. G. (1982) Biochemistry 21, 2285-2292.
22. Bode, W., Mayr, I., Baumann, U., Huber, R., Stone, S. R. & Hofsteenge, J. (1989) EMBO J. 8, 3467-3475.
23. Bode, W., Schwager, P. & Huber, I (1978) J. Mol. Biol. 118, 99-112.
24. Bode, W. & Huber, R. (1976) FEBS Lett. 68, 231-236.
25. Chen, Q. & Lentz, B. R. (1997) Biochemistry 36, 4701-4711.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A variant zymogen/protease which modulates hemostasis wherein said variant comprises amino acids 44-622 of the sequence of SEQ ID NO: 1 said variant containing at least one modification in SEQ ID NO: 1 selected from the group consisting of:
   a) Ile at position 364 is replaced with Thr, or Val;
   b) Val at position 365 is replaced with Ala, or Ile, or Glu and
   c) Glu at position 366 is replaced with Thr, or Gly.

2. The variant zymogen/protease of claim 1, wherein the amino acid sequence at positions 364-346 in SEQ ID NO: 1 is selected from the group consisting of Thr-Ala-Thr, Val-Ile-Glu and Ile-Glu-Gly.

3. A pharmaceutical composition comprising the variant zymogen/protease of claim 1 in a biologically compatible carrier.

4. A nucleic acid encoding the variant zymogen/protease of claim 1.

5. A nucleic acid as claimed in claim 4, wherein the nucleotides at positions 1121-1129 of SEQ ID NO: 2 encode amino acids selected from the group consisting of Thr-Ala-Thr, Val-Ile-Glu and Ile-Glu-Gly.

6. The variant zymogen/protease encoded by the nucleic acid of claim 5, present in a biologically compatible carrier.

7. The nucleic acid of claim 5 cloned into an expression vector.

8. The vector of claim 7, selected from the group consisting of an adenoviral vector, an adenovirus-associated vector, a retroviral vector, a plasmid, and a lentiviral vector.

9. A host cell expressing the vector of claim 7.

* * * * *

SEQUENCE LISTING

```
<160> NUMBER OF SEQ ID NOS: 5

<210> SEQ ID NO 1
<211> LENGTH: 622
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (364)...(366)
<223> OTHER INFORMATION: Xaa = any amino acid

<400> SEQUENCE: 1

Met Ala His Val Arg Gly Leu Gln Leu Pro Gly Cys Leu Ala Leu Ala
 1               5                  10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60
```

```
Cys Ser Tyr Glu Glu Ala Phe Glu Ala Leu Glu Ser Ser Thr Ala Thr
 65                  70                  75                  80

Asp Val Phe Trp Ala Lys Tyr Thr Ala Cys Glu Thr Ala Arg Thr Pro
                 85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
130                 135                 140

Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Xaa Xaa Xaa Gly Ser
        355                 360                 365

Asp Ala Glu Ile Gly Met Ser Pro Trp Gln Val Met Leu Phe Arg Lys
370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
```

```
              485                 490                 495
Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
            515                 520                 525

Pro Ile Val Glu Arg Pro Val Cys Lys Asp Ser Thr Arg Ile Arg Ile
            530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
            595                 600                 605

Leu Lys Lys Trp Ile Gln Lys Val Ile Asp Gln Phe Gly Glu
        610                 615                 620

<210> SEQ ID NO 2
<211> LENGTH: 1997
<212> TYPE: DNA
<213> ORGANISM: Artificial Sequence
<220> FEATURE:
<223> OTHER INFORMATION: Synthetic Sequence

<400> SEQUENCE: 2
aattcctcag tgacccagga gctgacacac tatggcgcac gtccgaggct tgcagctgcc      60
tggctgcctg gccctggctg ccctgtgtag ccttgtgcac agccagcatg tgttcctggc     120
tcctcagcaa gcacggtcgc tgctccagcg ggtccggcga ccaacacct tcttggagga     180 ggtgcgcaag gcaacctgg agcgagagtg cgtggaggag acgtgcagct acgaggaggc     240
cttcgaggct ctggagtcct ccacggctac ggatgtgttc tgggccaagt acacagcttg     300
tgagacagcg aggacgccac gagataagct tgctgcatgt ctggaaggta actgtgctga     360
gggtctgggt acgaactacc gagggcatgt gaacatcacc cggtcaggca ttgagtgcca     420
gctatggagg agtcgctacc cacataagcc tgaaatcaac tccactaccc atcctggggc     480
cgacctacag gagaatttct gccgcaaccc cgacagcagc accacgggac cctggtgcta     540
cactacagac cccaccgtga ggaggcagga atgcagcatc cctgtctgtg ccaggatca     600 agtcactgta gcgatgactc cacgctccga aggctccagt gtgaatctgt cacctccatt     660
ggagcagtgt gtccctgatc gggggcagca gtaccagggg cgcctggcgg tgaccacaca     720
tgggctcccc tgcctggcct gggccagcgc acaggccaag gccctgagca agcaccagga     780
cttcaactca gctgtgcagc tggtggagaa cttctgccgc aacccagacg ggatgagga     840 gggcgtgtgg tgctatgtgg ccgggaagcc tggcgacttt gggtactgcg acctcaacta     900
ttgtgaggag gccgtggagg aggagacagg agatgggctg gatgaggact cagacagggc     960
catcgaaggc cgtaccgcca ccagtgagta ccagactttc ttcaatccga ggaccctttgg    1020 ctcgggagag gcagactgtg ggctgcgacc tctgttcgag aagaagtcgc tggaggacaa    1080
aaccgaaaga gagctcctgg aatcctacat cgacgggcgc attgtggagg ctcggatgc     1140 agagatcggc atgtcacctt ggcaggtgat gcttttccgg aagagccccc aggagctgct    1200 gtgtgggggcc agcctcatca gtgaccgctg gtcctcacc gccgcccact gcctcctgta    1260
cccgccctgg gacaagaact tcaccgagaa tgaccttctg gtgcgcattg gcaagcactc    1320
```

-continued

```
ccgcaccagg tacgagcgaa acattgaaaa gatatccatg ttggaaaaga tctacatcca    1380
ccccaggtac aactggcggg agaacctgga ccgggacatt gccctgatga agctgaagaa    1440
gcctgttgcc ttcagtgact acattcaccc tgtgtgtctg cccgacaggg agacggcagc    1500
cagcttgctc caggctggat acaaggggcg ggtgacaggc tggggcaacc tgaaggagac    1560
gtggacagcc aacgttggta aggggcagcc cagtgtcctg caggtggtga acctgcccat    1620
tgtggagcgg ccggtctgca aggactccac ccgtatccgc atcactgaca acatgttctg    1680
tgctggttac aagcctgatg aagggaaacg aggggatgcc tgtgaaggtg acagtggggg    1740 acctttgtc atgaagagcc cctttaacaa ccgctggtat caaatgggca tcgtctcatg    1800
gggtgaaggc tgtgaccggg atgggaaata tggcttctac acacatgtgt tccgcctgaa    1860
gaagtggata cagaaggtca ttgatcagtt tggagagtag tgataactcg aggtaccgga    1920
tcctggaacc aatcccgtga agaattatt tttgtgtttc taaaactatg gttcccaata    1980
aaagtgactc tcagcgg                                                    1997
```

<210> SEQ ID NO 3
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 3

Lys Leu Ala Ala Ala Leu Glu His His His His His His
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 4

Ile Val Gly Gly
1

<210> SEQ ID NO 5
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 5

Arg Lys Arg Arg Lys Arg
1               5